United States Patent [19]

Hiraishi et al.

[11] Patent Number: 5,527,266

[45] Date of Patent: Jun. 18, 1996

[54] POLYURETHANE RESIN COMPOSITION AND SURGICAL CASTING TAPE THEREWITH

[75] Inventors: Kouzou Hiraishi; Nobuyasu Nakasugi, both of Kyoto-fu, Japan

[73] Assignee: San-Apro Limited, Kyoto-fu, Japan

[21] Appl. No.: 254,305

[22] Filed: Jun. 6, 1994

[30] Foreign Application Priority Data

Jun. 22, 1993 [JP] Japan .................................. 5-150206

[51] Int. Cl.[6] ........................................................ A61F 5/00
[52] U.S. Cl. ................................................. 602/8; 602/44
[58] Field of Search ................................. 602/5, 6, 7, 8, 602/9, 10, 11, 44; 128/90; 258/53

[56] References Cited

U.S. PATENT DOCUMENTS

| | | | |
|---|---|---|---|
| 4,075,185 | 2/1979 | Kray | 260/79.3 |
| 4,241,199 | 12/1980 | Dunleavy | 525/445 |
| 4,469,831 | 9/1984 | Bueltjer et al. | |
| 4,574,793 | 3/1986 | Lee et al. | |
| 4,705,840 | 11/1987 | Buckanin | 528/53 |
| 5,244,997 | 9/1993 | Scholz et al. | 602/6 |
| 5,324,252 | 6/1994 | Libbey et al. | 602/5 |

Primary Examiner—Corrine M. Maglione
Assistant Examiner—N. Kent Gring
Attorney, Agent, or Firm—McAulay Fisher Nissen Goldberg & Kiel

[57] ABSTRACT

Proposed is a moisture-curable polyurethane resin composition having good storage stability under a moisture-free condition without affecting the curability in the presence of moisture. The composition comprises (a) a polyurethane prepolymer as a reaction product of a polyol compound and a polyisocyanate compound, (b) a catalytic compound to promote curing of the composition and (c) a stabilizer which is trifluoromethane sulfonic acid in a limited amount. The improvement in the storage stability of the composition is particularly remarkable when trifluoromethane sulfonic acid is used in combination with a specific curing catalyst. The composition is useful in the preparation of a surgical casting tape by coating or impregnating a flexible substrate web such as a glass fiber cloth therewith.

7 Claims, No Drawings

POLYURETHANE RESIN COMPOSITION AND SURGICAL CASTING TAPE THEREWITH

BACKGROUND OF THE INVENTION

The present invention relates to a curable polyurethane resin composition and a casting tape for surgery prepared by using the same. More particularly, the invention relates to a moisture-curable polyurethane resin composition having improved storage stability and suitable as an adhesive, sealant and coating composition as well as for use in the preparation of a casting tape for surgery.

As is well known, polyurethane resin compositions are used in a very wide field of applications in the preparation of, for example, coating compositions, sealants, adhesives, artificial leathers, resin rollers and the like. Curable polyurethane resin compositions are supplied either in the form of a one-package product, which is a blend of all of the necessary ingredients and curable when exposed to a moisture-containing atmosphere, or in the form of a two-package product, which is supplied in two packages each containing different ingredients to be blended together immediately before use so as to start the curing reaction. The one-package type polyurethane resin compositions are preferred to the two-package type products because of the easiness in handling not requiring exact weighing and mixing of the contents of the two packages before use to be freed from the troubles due to errors in weighing and incomplete mixing not to obtain full and even exhibition of the properties of the cured resin composition. In particular, casting tapes used as a plaster bandage in surgery are prepared by using a moisture-curable polyurethane resin composition of the one-package type.

Namely, traditional plaster bandages prepared by impregnating a loosely woven cloth such as gauze with calcined gypsum are under continuous replacement with a polyurethane resin-based casting tape prepared by impregnating a flexible substrate such as a glass fiber cloth with a moisture-curable polyurethane resin composition having a pasty consistency. Such a polyurethane resin-based surgical casting tape is stored under a hermetically sealed condition and, when the casting tape is taken out and wound around the affected part of the patient, curing reaction of the polyurethane resin composition proceeds by contacting with water or moisture in the air.

Various types of moisture-curable polyurethane resin compositions have been proposed for use in the preparation of the above described surgical casting tapes including those polyurethane prepolymers consisting of an aromatic polyisocyanate and a polyol disclosed, for example, in Japanese Patent Kokai 54-100181 and elsewhere.

While it is usual that a moisture-curable polyurethane resin composition is admixed with a catalyst to promote the curing reaction of the resin composition when it is contacted with moisture, a problem in the use of a curing catalyst is that the storage stability of the polyurethane resin composition is decreased thereby to cause premature curing or gelation of the composition during storage so that it is also usual to compound the moisture-curable polyurethane resin composition with a stabilizer. Accordingly, a proper choice of the combination of a curing catalyst and a stabilizer is very important in a moisture-curable polyurethane resin composition and a surgical casting tape prepared therewith. For example, U.S. Pat. No. 4,433,680 proposes dimorpholino diethyl ether as the curing catalyst and benzoyl chloride as the stabilizer and U.S. Pat. No. 4,574,793 proposes bis(2,6-dimethylmorpholino) diethyl ether as the curing catalyst and methane sulfonic acid as the stabilizer. These prior art formulations, however, are not always quite satisfactory in respect of the balance of the curability and the stabilizing effect because satisfactory storage stability can hardly be obtained without affecting the curability of the composition. Thus, it is eagerly desired to develop a moisture-curable polyurethane resin composition having excellent storage stability without substantially affecting the curability of the composition.

SUMMARY OF THE INVENTION

The present invention accordingly has an object to provide a moisture-curable polyurethane resin composition having greatly improved storage stability without decreasing the curability as good as in the prior art compositions. The invention also has an object to provide a surgical casting tape prepared by using the polyurethane resin composition as an impregnant or a coating material of a substrate having flexibility.

Thus, the moisture-curable polyurethane resin composition provided by the present invention is a uniform blend which comprises:

(a) a polyurethane prepolymer which is a reaction product of a polyol compound and a polyisocyanate compound;

(b) a catalytic compound which promotes the curing reaction of the polyurethane prepolymer in the presence of moisture; and (c) trifluoromethane sulfonic acid in an amount in the range from 0.005% to 1% by weight or, preferably, from 0.01% to 0.1% by weight based on the total amount of the composition consisting of the components (a), (b) and (c).

The stabilizing effect of the polyurethane resin composition obtained by the admixture of trifluoromethane sulfonic acid as the component (c) is most remarkable when the catalytic compound as the component (b) is a morpholinoethyl ether compound or, in particular, bis[2-(4-morpholino)propyl] ether or bis[2-{4-(2,6-dimethylmorpholino)}propyl] ether.

The present invention further provides a casting tape for surgery which comprises:

(A) a sheet material having flexibility as a substrate; and (B) a coating layer on the substrate formed from a moisture-curable polyurethane resin composition which is a uniform blend as defined above.

DETAILED DESCRIPTION OF THE PREFERRED EMBODIMENTS

As is described above, the essential ingredients in the moisture-curable polyurethane resin composition of the present invention includes a polyurethane prepolymer as the component (a), a catalytic compound as the component (b) which promotes the curing reaction of the composition and trifluoromethane sulfonic acid as the component (c) which serves as a stabilizer to improve the storage stability of the composition.

The base ingredient in the inventive moisture-curable polyurethane resin composition is a polyurethane prepolymer which is a reaction product of a polyol compound and a polyisocyanate compound. Examples of suitable polyol compounds include low molecular polyol compounds such as ethyleneglycol, propyleneglycol and glycerin, polyether polyol compounds as an addition product of an alkylene oxide such as ethylene oxide and propylene oxide to a low-molecular polyol compound, polyphenol compound, e.g., hydroquinone and bisphenol A, or an amine compound, e.g., aniline, ethylene diamine and diethylene triamine, polyester polyol compounds obtained by the dehydration condensation reaction between a low-molecular polyol compound and a dibasic carboxylic acid, e.g., adipic acid and phthalic acid, polylactone polyol compound obtained by the ring-opening polymerization of a lactone, e.g., γ-butyrolactone and ε-caprolactone, polytetramethylene glycol obtained by the ring-opening polymerization of tetrahydrofuran, castor oil and an alkylene oxide adduct thereof, polydiene polyol compounds as a polymer of a diene compound such as butadiene and isoprene having a hydroxyl group at each molecular chain end as well as a hydrogenation product thereof, and so on. These polyol compounds can be used either singly or as a combination of two kinds or more according to need. It is preferable to use a polyol compound having an average molecular weight in the range from 200 to 4000 or, more preferably, from 400 to 4000.

As to the polyisocyanate compound to be reacted with the above described polyol compound, various kinds of known polyisocyanate compounds can be used without particular limitations. Examples of suitable polyisocyanate compounds include aromatic polyisocyanate compounds such as 2,4-tolylene diisocyanate, 2,6-tolylene diisocyanate, 4,4'-diphenylmethane diisocyanate, 2,4'-diphenylmethane diisocyanate, 1,4-phenylene diisocyanate and polymethylene polyphenylene polyisocyanates, aliphatic polyisocyanate compounds such as hexamethylene diisocyanate, alicyclic polyisocyanate compounds such as 3-isocyanatomethyl-3,5,5-trimethyl cyclohexyl isocyanate and aryl-substituted aliphatic polyisocyanate compounds such as xylylene diisocyanate, as well as those polyisocyanate compounds obtained by the modification thereof with carbodiimide or isocyanurate, and so on. These polyisocyanate compounds can be used either singly or as a combination of two kinds or more according to need.

The polyurethane prepolymer can be obtained by heating a mixture of the polyol compound and the polyisocyanate compound at a temperature in the range from 30° to 120° C. under agitation for 1 to 10 hours. The blending ratio of the polyol compound and the polyisocyanate compound should be such that, when a polyurethane prepolymer having an isocyanate group at the molecular chain end is desired, the polyisocyanate compound contains from 1.2 to 10 moles or, preferably, from 2.5 to 5 moles of the isocyanate groups per mole of the hydroxyl groups in the polyol compound.

The curing catalyst as the component (b) in the inventive polyurethane resin composition can be any of known ones including morpholinoethyl ether compounds exemplified by dimorpholino diethyl ether, bis(2,6-dimethylmorpholino) diethyl ether and substituted morpholino diethyl ether disclosed in U.S. Pat. No. 4,705,840 but it is desirable that the storage stability of the polyurethane resin composition is not unduly decreased by the admixture of the curing catalyst under a moisture-free condition. Examples of particularly preferable catalytic compounds include bis[2-(4-morpholino)propyl] ether and bis[2-{4-(2,6-dimethylmorpholino)}propyl] ether when used in combination with the specific stabilizer proposed in the present invention. The amount of the catalytic compound compounded in the moisture-curable polyurethane resin composition is in the range from 0.1% to 3.0% by weight based on the total amount of the polyurethane resin composition.

The component (c) in the inventive resin composition is trifluoromethane sulfonic acid which serves as a stabilizer to prevent premature curing or gelation of the polyurethane resin composition stored under a moisture-free condition. Any commercially available products of trifluoromethane sulfonic acid can be used as such without further purification. The amount of the component (c) in the inventive polyurethane resin composition is in the range, usually, from 0.005% to 1% by weight or, preferably, from 0.01% to 0.1% by weight based on the total amount of the components (a), (b) and (c) although an optimum amount depends on the type and amount of the curing catalyst as the component (b). When the amount of the stabilizer is too small, the desired stabilizing effect cannot be obtained as a matter of course while, when the amount thereof is too large, the curability of the composition is adversely affected.

The moisture-curable polyurethane resin composition can be prepared by uniformly blending the component (a), i.e. the polyurethane prepolymer as a reaction product of a polyol compound and a polyisocyanate compound, component (b), i.e. the curing catalyst, and component (c), i.e. the stabilizer, each in a specified weight proportion. It is optional that the composition is further admixed with various kinds of known additives according to need including antifoam agents, antioxidants, ultraviolet absorbers, coloring agents, e.g., dyes and pigments, fillers, e.g., calcium carbonate, titanium dioxide, carbon black, clay and the like, and so on each in a limited amount. Alternatively, it is optional that these additives are admixed partly or wholly with the reaction mixture of the polyol compound and the polyisocyanate compound in the preparation of the polyurethane prepolymer together with the curing catalyst and the stabilizer.

The moisture-curable polyurethane resin composition of the present invention can be stored with stability for a long period of time when kept in a hermetically sealable container, from which the composition is taken out for use by coating or impregnation so that curing of the composition proceeds by exposure to the moisture-containing atmosphere.

When the intended application of the inventive moisture-curable polyurethane resin composition is as an impregnant of a surgical casting tape, it is preferable that the polyurethane prepolymer is prepared from a polyol compound which is a low-molecular diol compound or a polyether diol compound by the addition of an alkylene oxide to bisphenol A either alone or in combination. Examples of particularly preferable polyol compounds include poly(oxyethylene) glycols, poly(oxypropylene) glycols and random—or block-copolymeric poly(oxyethylene-oxypropylene) glycols having an average molecular weight of 400 to 4000, adducts of 2 to 30 moles of propylene oxide to mole of bisphenol A and adducts of 2 to 3 moles of ethylene oxide to mole of bisphenol A.

Examples of preferable polyisocyanate compounds, when the intended application of the inventive moisture-curable polyurethane resin composition is as an impregnant of a surgical casting tape, include aromatic polyisocyanate compounds or, in particular, 4,4'-diphenylmethane diisocyanate, 2,4'-diphenylmethane diisocyanate and 1,4-phenylene diisocyanate modified or unmodified with carbodiimide.

The blending ratio of the above described particular polyol compound and polyisocyanate compound is such that the polyisocyanate compound contains, usually, from 2 to 5 moles or, preferably, from 2.5 to 4 moles of the isocyanate groups per mole of the hydroxyl groups in the polyol compound.

The polyurethane prepolymer should have an appropriate viscosity depending on the particular application of the polyurethane resin composition. For example, the viscosity should be in the range from 5000 to 100,000 centipoise or, preferably, from 10,000 to 50,000 centipoise at room temperature when it is the base ingredient of the inventive composition to be used as an impregnant of a surgical casting tape while the viscosity should be in the range from 2,000 to 10,000 centipoise for a coating composition, from 5,000 to 20,000 centipoise for an adhesive and from 10,000 to 200,000 centipoise for a sealant. Other property parameters of the prepolymer can be approximately the same as in the polyurethane prepolymers used in the preparation of moisture-curable polyurethane resin compositions in general employed in other applications.

The surgical casting tape of the invention can be prepared by coating or impregnating a flexible substrate sheet, which is preferably a glass fiber cloth, with the above described moisture-curable polyurethane resin composition by using a suitable coating machine such as roller coaters or by dipping in the resin composition followed by squeezing off of the extraneous portion of the resin composition by using squeezer rollers. The thus completed surgical casting tape is stored in a hermetically sealable container or bag to be prevented from contacting with moisture-containing atmosphere.

In the following, the moisture-curable polyurethane resin composition and the surgical casting tape of the present invention are illustrated in more detail by way of examples and comparative examples. In the following, the term of "parts" always refers to "parts by weight".

EXAMPLE 1

A polyurethane resin composition was prepared in the following manner. Thus, 277 parts of a first polyoxypropylene glycol having an average molecular weight of 700 (Exenol 720, a product by Asahi Glass Co.) and 118 parts of a second polyoxypropylene glycol having an average molecular weight of 400 (Sannix PP 400, a product by Sanyo Chemical Industries Co.) were mixed together with admixture of 1 part of an antioxidant (tetrakis[methylene-3-(3',5'-di-tert-butyl-4'-hydroxyphenyl) propionate] methane, Irganox 1010, a product by Ciba-Geigy Co.) and 1 part of an antifoam agent (Byk-A 525, a product by Byk Chemie Japan Co.) at 100° to 110° C. under reduced pressure. The average molecular weight of the polyol ingredients was 572. After cooling to room temperature, the polyol mixture was admixed with 544 parts of 4,4'-diphenylmethane diisocyanate (Isonate 125M, a product by Mitsubishi Kasei Dow Co.) and agitated for three hours at 70° to 80° C. After cooling to 50° to 60° C., the mixture was further admixed with 18 parts of bis(2,6-dimethylmorpholino)ethyl ether as a curing catalyst, 0.7 part of trifluoromethane sulfonic acid (a product by Wako Pure Chemical Industries Co.) as a stabilizer and 40 parts of a tackiness reducing agent (polyethylene glycol distearate, Nonion S-40, a product by Daiichi Kogyo Seiyaku Co.) and the mixture was further agitated for two hours to give a completed polyurethane resin composition.

The thus obtained moisture-curable polyurethane resin composition was subjected to the tests of viscosity, content of the isocyanate groups —NCO, storage stability and curing time by the procedures described below to give the results shown in Table 1.

Viscosity:

Viscosity of the composition was determined at 20° C. by using a rotational viscosimeter with the No. 4 rotor rotated at 12

Content of isocyanate groups:

The composition was reacted with an amine solution followed by back-titration of the unreacted amine with a calibrated hydrochloric acid solution according to the procedure specified in JIS K 1603.

Storage stability:

An about 50 ml portion of the polyurethane resin composition was taken in a polypropylene bottle of 100 ml capacity and hermetically sealed therein under an atmosphere of dry nitrogen gas. The bottle was kept in an oven controlled at 130° C. and the length of time was recorded until the resin composition contained therein was no longer flowable.

Curing time:

A surgical casting tape was prepared by coating and impregnating a warp-knit glass fiber tape having counts of 14 warps/inch and 15 wefts/inch and a basis weight of 310 $g/m^2$ with the above prepared polyurethane resin composition in an amount of 210 $g/m^2$ in an atmosphere of dry air. The thus prepared surgical casting tape in a length of 3.6 meters was wound around a core mandrel of 2 cm diameter to form a roll which was stored in a hermetically sealable bag of an aluminum foil-laminated polyethylene sheet by heat sealing. The casting tape taken out of the bag as wound around the core mandrel was dipped in water at 20° C. for 10 seconds. After being freed from water drops and standing as such for a length of time, the tape was unwound from the mandrel and again wound around a cylindrical rod of 3 inches outer diameter to record the length of the standing time as the adaptability time until the casting tape could no longer be wound around the cylindrical rod. The result is shown in Table 1.

EXAMPLE 2

The formulation of the moisture-curable polyurethane resin composition and the testing procedures thereof were substantially the same as in Example 1 except that bis(2,6-dimethylmorpholino)ethyl ether as the curing catalyst was replaced with the same amount of bis[2-(4-morpholino)propyl] ether. The results of the evaluation tests were as shown in Table 1.

EXAMPLE 3

The formulation of the moisture-curable polyurethane resin composition and the testing procedures thereof were substantially the same as in Example 1 except that bis(2,6-dimethylmorpholino)ethyl ether as the curing catalyst was replaced with the same amount of bis[2-{4-(2,6-dimethylmorpholino)}propyl] ether. The results of the evaluation tests were as shown in Table 1.

EXAMPLE 4

The formulation of the moisture-curable polyurethane resin composition and the testing procedures thereof were substantially the same as in Example 2 except that the amount of the trifluoromethane sulfonic acid as the stabilizer was decreased from 0.7 part to 0.1 part. The results of the evaluation tests were as shown in Table 1.

EXAMPLE 5

The formulation of the moisture-curable polyurethane resin composition and the testing procedures thereof were substantially the same as in Example 2 except that the amount of the trifluoromethane sulfonic acid as the stabilizer was decreased from 0.7 part to 0.5 part and 18 parts of bis[2-(4-morpholino)propyl] ether as the curing catalyst were replaced with a combination of 9 parts of the same compound and 9 parts of bis[2-{4-(2,6-dimethylmorpholino)}propyl] ether. The results of the evaluation tests were as shown in Table 1.

EXAMPLE 6

The formulation of the moisture-curable polyurethane resin composition and the testing procedures thereof were substantially the same as in Example 2 except that the amount of the trifluoromethane sulfonic acid as the stabilizer was increased from 0.7 part to 1.0 part. The results of the evaluation tests were as shown in Table 1.

COMPARATIVE EXAMPLE 1

The formulation of the moisture-curable polyurethane resin composition and the testing procedures thereof were substantially the same as in Example 2 except that 0.7 part of trifluoromethane sulfonic acid as the stabilizer was replaced with 2.0 parts of benzoyl chloride (a product by Wako Pure Chemical Industries Co.). The results of the evaluation tests were as shown in Table 1.

COMPARATIVE EXAMPLE 2

The formulation of the moisture-curable polyurethane resin composition and the testing procedures thereof were substantially the same as in Example 2 except that trifluoromethane sulfonic acid as the stabilizer was replaced with the same amount of methane sulfonic acid (a product by Wako Pure Chemical Industries Co.). The results of the evaluation tests were as shown in Table 1.

COMPARATIVE EXAMPLE 3

The formulation of the moisture-curable polyurethane resin composition and the testing procedures thereof were substantially the same as in Example 2 except that trifluoromethane sulfonic acid as the stabilizer was replaced with the same amount of methane sulfonic acid chloride (a product by Wako Pure Chemical Industries Co.). The results of the evaluation tests were as shown in Table 1.

COMPARATIVE EXAMPLE 4

The formulation of the moisture-curable polyurethane resin composition and the testing procedures thereof were substantially the same as in Example 2 except that trifluoromethane sulfonic acid as the stabilizer was replaced with the same amount of trifluoroacetic acid (a product by Wako Pure Chemical Industries Co.). The results of the evaluation tests were as shown in Table 1.

COMPARATIVE EXAMPLE 5

The formulation of the moisture-curable polyurethane resin composition and the testing procedures thereof were substantially the same as in Example 2 except that the amount of the trifluoromethane sulfonic acid as the stabilizer was decreased from 0.7 part to 0.01 part. The results of the evaluation tests were as shown in Table 1.

TABLE 1

| | Viscosity, centipoise | NCO content, % | Storage stability, hours | Curing time, seconds |
|---|---|---|---|---|
| Example 1 | 21200 | 11.4 | 66 | 145–150 |
| Example 2 | 22000 | 11.5 | 73 | 140–145 |
| Example 3 | 21500 | 11.2 | 72 | 142–147 |
| Example 4 | — | — | 70 | 130–135 |
| Example 5 | — | — | 73 | 135–140 |
| Example 6 | — | — | 74 | 145–150 |
| Comparative Example 1 | 22500 | 11.0 | 40 | 145–150 |
| Comparative Example 2 | 21400 | 11.3 | 60 | 145–150 |
| Comparative Example 3 | 23300 | 11.4 | 48 | 140–145 |
| Comparative Example 4 | 20800 | 11.3 | 54 | 142–157 |
| Comparative Example 5 | — | — | 20 | 120–130 |

The above data shows that with the inventive compositions, enhanced storage stability is obtained without any adverse effect on curing time whereas for compositions outside the inventive ranges, storage stability is adversely effected.

What is claimed is:

1. A moisture-curable polyurethane resin composition which comprises, as a uniform blend:
   (a) a polyurethane prepolymer which is a reaction product of a polyol compound and a polyisocyanate compound;
   (b) a catalytic compound which promotes a curing reaction of the polyurethane prepolymer in the presence of moisture; and
   (c) trifluoromethane sulfonic acid in an amount from 0.005% to 1% by weight based on the total weight of the composition.

2. The moisture-curable polyurethane resin composition as claimed in claim 1 in which the amount of the trifluoromethane sulfonic acid as the component (c) is from 0.01% to 0.1% by weight based on the total weight of the composition.

3. The moisture-curable polyurethane resin composition as claimed in claim 1 in which the catalytic compound is a morpholinoethyl ether compound.

4. The moisture-curable polyurethane resin composition as claimed in claim 1 in which the catalytic compound is bis[2-(4-morpholino)propyl] ether or bis[2-{4-(2,6-dimethylmorpholino)}propyl] ether.

5. The moisture-curable polyurethane resin composition as claimed in claim 1 in which the amount of component (b) is from 0.1% to 3% by weight based on the total weight of the composition.

6. A casting tape for surgery which comprises:
   (A) a flexible substrate sheet; and
   (B) a coating layer on the substrate sheet consisting of a moisture-curable polyurethane resin composition comprising, as a uniform blend:
   (a) a polyurethane prepolymer which is a reaction product of a polyol compound and a polyisocyanate compound;
   (b) a catalytic compound which promotes a curing reaction of the polyurethane prepolymer in the presence of moisture; and
   (c) trifluoromethane sulfonic acid in an amount from 0.005% to 1% by weight based on the total weight of the composition.

7. The casting tape for surgery as claimed in claim 6 in which the flexible substrate sheet is a glass fiber cloth.

* * * * *